(12) United States Patent
Scardina et al.

(10) Patent No.: US 10,352,767 B2
(45) Date of Patent: Jul. 16, 2019

(54) COLOR MEASUREMENT SYSTEMS, DEVICES, AND METHODS

(71) Applicant: Hunter Associates Laboratory, Inc., Reston, VA (US)

(72) Inventors: Michael T. Scardina, Woodbridge, VA (US); Tod L. Kerr, Reston, VA (US); Miguel A. Marcos, Falls Church, VA (US); Greg L. Howell, Reston, VA (US)

(73) Assignee: HUNTER ASSOCIATES LABORATORY, INC., Reston, VA (US)

( * ) Notice: Subject to any disclaimer, the term of this patent is extended or adjusted under 35 U.S.C. 154(b) by 0 days.

(21) Appl. No.: 16/016,130

(22) Filed: Jun. 22, 2018

(65) Prior Publication Data

US 2018/0372541 A1 Dec. 27, 2018

Related U.S. Application Data

(60) Provisional application No. 62/523,886, filed on Jun. 23, 2017.

(51) Int. Cl.
*G01J 3/46* (2006.01)
*G01J 3/02* (2006.01)
*G01J 3/50* (2006.01)
*G01J 3/10* (2006.01)
*G01N 21/25* (2006.01)

(52) U.S. Cl.
CPC ............. *G01J 3/0289* (2013.01); *G01J 3/027* (2013.01); *G01J 3/0237* (2013.01); *G01J 3/0264* (2013.01); *G01J 3/0278* (2013.01); *G01J 3/0291* (2013.01); *G01J 3/10* (2013.01); *G01J 3/501* (2013.01); *G01N 21/251* (2013.01); *G01J 2003/102* (2013.01)

(58) Field of Classification Search
CPC ........ G01J 3/02; G01J 3/50; G01J 3/10; G01J 3/46; G01J 3/42; G01N 21/27; G01N 21/57; B29C 67/00
See application file for complete search history.

(56) References Cited

U.S. PATENT DOCUMENTS

2015/0061170 A1\* 3/2015 Engel .................... B33Y 10/00
264/40.1

\* cited by examiner

*Primary Examiner* — Abdullahi Nur
(74) *Attorney, Agent, or Firm* — W & C IP

(57) ABSTRACT

Color measurement instruments and processes provide automated and accurate color measurements. Sensor to sample distance is automatically adjusted by the instrument over the course of measurement collection. Adaptive parameters may include turntable speed, illumination spectrum, laser gain setting, number of measurement samples, duration of sampling, sample color measurement threshold, and distance variation measurement threshold.

21 Claims, 18 Drawing Sheets

COLOR MEASUREMENT SYSTEMS, DEVICES, AND METHODS

CROSS-REFERENCE TO RELATED APPLICATIONS

This application claims the benefit of U.S. provisional patent application No. 62/523,886, filed Jun. 23, 2017, the complete contents of which are herein incorporated by reference.

FIELD OF THE INVENTION

The invention generally relates to color measurement and, in particular, systems, devices, and methods which improve the accuracy and reproducibility of color measurements taken from any of a variety of sample types.

BACKGROUND

Three elements are involved in seeing or perceiving color: a light source, an object, and an observer. A framework of describing human color perception according to these three elements is sometimes referred to as the visual observing situation. To build an instrument that quantifies human color perception, each item in the visual observing situation may be characterized.

The first element of the visual observing situation is a light source. A light source is a physical source of light. The visible portion of the electromagnetic spectrum is defined by the International Commission on Illumination (CIE) as 360 to 780 nm. A plot of the relative energy at each wavelength creates a spectral power distribution curve that quantifies the characteristics of the light source. A CIE illuminant is a standard table of numbers representing relative energy versus wavelength for the spectral characteristics of light sources. Some common illuminants and their CIE abbreviations are as follows: Incandescent (A), Average Daylight (C), Noon Daylight ($D_{65}$), and Cool White Fluorescent (F2). By representing a light source as an illuminant, the spectral characteristics of the first element of the visual observing situation is quantified and standardized.

The second element of the visual observing situation is an object. Objects modify light. Colorants such as pigments or dyes that are in or on the object selectively absorb some wavelengths of incident light while reflecting or transmitting other wavelengths. The amount of light that is reflected, absorbed, or transmitted by the object at each wavelength can be quantified. This can be represented as a spectral curve. By measuring the relative reflectance or transmission characteristics of an object, the second element of the visual observing situation becomes quantified. Relative reflectance, or reflectance factor, is defined as the relative amount of energy measured on an arbitrary sample at a fixed geometry, in reflection, with respect to a known white sample similarly used to define the top-of-scale of the measurement. This is important to distinguish as reflectivity is also a function of angle and total reflectance would require a hemisphere to collect all angles. A device which measures relative reflectance or transmittance as a function of wavelength is typically a spectrophotometer.

The third element of the visual observing situation is the observer, which is often but not necessarily a human. A human eye has structures referred to as rods and cones. Cones are responsible for color vision and have three types of sensitivity: red, green, and blue. The CIE experimentally measured the ability of the human eye to perceive color. The experimentally derived x-bar, y-bar, and z-bar functions became the CIE 1931 2° Standard Observer. The functions x-bar, y-bar, and z-bar quantify the red, green, and blue cone sensitivity of an average human observer. An updated standard was later produced and is referred to as the 1964 10° Standard Observer. This is the standard recommended for use today by the CIE.

In science and industry, the trifecta of light source, object, and observer becomes the trifecta of light source, sample, and spectrophotometer. The CIE X, Y, and Z tristimulus color values are obtained by multiplying the illuminant, the reflectance or transmittance of the object, and the standard observer functions. The product is then summed for all wavelengths in the visible spectrum to give the resulting X, Y, Z tristimulus values.

A colorimetric spectrophotometer may comprise a light source, a diffraction grating, a diode array, and a processor. The instrument may be configured to produce CIE X, Y, Z color values for a sample. Briefly, the light source illuminates the sample being measured. Light reflected by the objects is passed to a diffraction grating which breaks it into its spectral components. Much of the diffracted light falls onto the diode array which senses the amount of light at each wavelength. The spectral data is sent to the processor where it is multiplied with a user-selected illuminant and observer tables to obtain CIE X, Y, Z color values.

The CIE X, Y, Z value system is a color scale. When describing color, the CIE X, Y, Z values are not easily understood (they are not intuitive). Other color scales have been developed to better relate to how humans perceive color, simplify understanding of the metrics, improve communication of color, and better represent uniform color differences. All colors can be organized in three dimensions: lightness, chroma or saturation, and hue. Hunter L, a, b color space is a 3-dimensional rectangular color based on Opponent-Colors Theory with the following dimensions:

L (lightness) axis: 0 is black, 100 is white, and 50 is middle gray a (red-green) axis: positive values are red, negative values are green, and 0 is neutral b (blue-yellow) axis: positive values are yellow, negative values are blue, and 0 is neutral The opponent-colors have been explained physiologically by the organization of cone cells into what are called receptive fields in the fovea of the human eye. A receptive field provides a number of inputs from the cone cells (both positive and negative) that can interface with ganglion cells to produce spatial edge-detection for red-green and blue-yellow stimuli. The spectral distribution for these receptive fields correlates well with a, b.

There are two popular L, a, b color scales in use today: Hunter L, a, b and CIE L*, a*, b*. While similar in organization, a color will have different numerical values in these two color spaces. Both Hunter L, a, b and CIE L*, a*, b* scales are mathematically derived from CIE X, Y, Z values. Scales of chroma and hue are also functions of a* and b*; where chroma is the scalar magnitude, $((a^*)^2+(b^*)^2)^{1/2}$, and hue angle is represented by the arc tangent of (b*/a*).

Color measurement is employed in industry and in education according to color differences. Color differences are calculated as sample-standard values. According to the CIE L*, a*, b* color scale, If delta L* is positive, the sample is lighter than the standard. If delta L* is negative, the sample is darker than the standard.

If delta a* is positive, the sample is more red (or less green) than the standard. If delta a* is negative, the sample is more green (or less red) than the standard.

If delta b* is positive, the sample is more yellow (or less blue) than the standard. If delta b* is negative, the sample is more blue (or less yellow) than the standard.

Total color difference (delta E*, or ΔE*) is based on the L*, a*, b* color differences and was designed to be single number metric for PASS/FAIL decisions in industry. Delta E* is determined as the square root of the sum of the squares of L*, a*, and b*:

$$\Delta E^* = \sqrt{(\Delta L^*)^2 + (\Delta a^*)^2 + (\Delta b^*)^2}$$

Thus far color of an object or sample has been generally ascribed to pigments or dyes. Other qualities of an object also play a role in color, further complicating its measurement and characterization. Surface characteristics and geometry play an important role in color.

One surface characteristic of samples is reflectance. For opaque materials, most of the incident light is reflected. For translucent materials, most of the incident light is transmitted. Reflectance make take either of two forms. Diffuse reflection involves non-directional reflected light. This light is scattered in many directions. Specular reflection is reflection of light by which the angle of reflection matches the angle of incidence of the incident light striking the surface of the object.

Color is seen in the diffuse reflection, and gloss is seen in the specular reflection. The reflection at the specular angle is generally the greatest amount of light reflected at any single angle. From air-to-glass at low angles of incidence, specular reflection represents less than 4% of total incident light. For a 60° angle (as in gloss geometry), the reflection of polished glass is ~10%. The remaining light is transmitted or absorbed with almost no diffuse reflection.

Richard Sewall Hunter, a pioneer in color and appearance, identified six visual criteria for defining a gloss scale. These are specular gloss, contrast gloss, distinctness-of-image (DOI) gloss, absence-of-bloom gloss, sheen, and surface-uniformity gloss. In the color industry, "instrumental gloss" is the most common form of gloss measurement and correlates with Hunter's specular gloss criteria. The ratio of diffuse reflection (45° to the angle of incidence) to specular reflection (equal to the angle of incidence) if subtracted from unity is a measure of contrast gloss. An exemplary geometry for measuring instrumental gloss on most samples is 60° (i.e., 60/60, defined with respect to the surface normal of the sample). Another geometry (30/30) has combined multiple field angles with a diode array to quantify reflection haze and distinctness of reflected image (DORI). Correlates of a perceived gloss scale in a color appearance model (CAM) may be referred to as visual gloss.

Surface texture of samples can greatly affect perceived color. Samples which have exactly the same color to a spectrophotometer, but which have different surface textures, will appear to have different colors to a human observer. Surfaces may generally be described as glossy or matte. Glossy surfaces appear darker or more saturated. Matte surfaces appear lighter and less saturated. Increased surface roughness affects perceived color such that it appears lighter and less saturated. This is caused by mixing diffuse reflectance (where humans see pigment color) with increased scatter from specular reflectance (white). The rougher the surface, the greater the scatter of the specular reflectance.

Other surface characteristics such as complex spatial patterns also affect perceived color. The S-CIELAB model was designed as a spatial pre-processor to the standard color difference equations, to account for these complex color structures. This model was a first step for simulating color appearance. Since the opponent-color spaces like L*, a*, b* are differentiable, there exists a direct correlation to the spatial receptive field and spatial gradients of the L*, a*, b* values.

Instrument geometry defines the arrangement of light source, sample plane, and detector. There are two general categories of instrument geometries: Bi-directional (45°/0° or 0°/45° and diffuse (d/8° sphere). Bi-Directional 45°/0° geometry has illumination at a 45° angle and measurement at 0°. The reciprocal, 0°/45° geometry, has illumination at 0° and measurement at 45°. Both directional geometries by definition exclude the specular reflection in the measurement. This is sometimes indicated in numerical tables by the phrase, "specular excluded". Bi-Directional geometry measurements provide measurements that may correspond to visual changes in sample appearance due to changes in either pigment color or surface texture. To reduce the directionality of an arbitrary sample, the 45° illumination or detection may be revolved circumferentially around the sample in at least 12 equally spaced locations.

Diffuse (sphere) geometry instruments use a white coated sphere to diffusely illuminate a sample with 8° (d/8°) viewing. Measurements on a diffuse sphere instrument can be taken with the specular included or specular excluded. Specular included measurements negate surface differences and provide values which correspond to changes in actual color (as opposed to perceived color). Specular excluded measurements negate specular reflectance on very smooth surfaces, measuring only diffuse reflectance. For illustration, as between two surfaces painted with the same red paint, one surface having a matte finish and the other surface having a high gloss finish, the specular included measurement indicates no color difference. It quantifies only colorant differences and negates differences in surface finishes. In the specular excluded mode, the readings quantify appearance differences, similar to those from the direction (0°/45°) geometry instrument. Most diffuse geometry measurements are taken in the specular included mode.

Color appearance models (currently) describe qualities such as lightness, brightness, colorfulness, chroma, saturation, and hue. They may also be extended to include a gloss scale. All CAMs rely on an opponent color space such as L*, a*, b*. The L*, a*, b* space, in particular, already quantifies lightness, chroma, saturation, and hue. For this reason, it is well-suited for application in CAM. The lightness and chroma can be scaled to provide brightness and colorfulness.

Glossmeters, spectrophotometers, and other devices employed in optics are traditionally independent instruments. These devices may be specially tailored to detect and characterize very specific qualities of the visual observing situation (e.g., gloss, reflectance, measured color, perceived color, and texture).

While specialized instruments exist for characterizing and quantifying color, achieving high levels of accuracy and reproducibility is difficult for when the instruments are subjected to use with a variety of different sample types or with heterogeneous samples. One sample type to the next (e.g., a cracker versus a cookie) may dramatically different in characteristics which can affect color measurement. Within even a single sample, properties may differ due to sample heterogeneity (e.g., variable shape, color, and size of parts of a chocolate chip cookie, or multiple cookies separated by aluminum space on a tray). Instruments and methods are needed which offer adaptive parameters and operation to accommodate sample type differences and sample differences without compromising accuracy and reproducibility of the color measurements.

SUMMARY

Some exemplary embodiments of the invention are directed to color measurement systems, in particular non-contact color measuring spectrophotometers and processes related thereto.

Some exemplary embodiments comprise control systems and processes for automated operation of spectrophotometers and color measuring instruments generally. Feedback loops may be provided which change parameters of a color measurement instrument based on real time measurements of distance and/or color.

Some exemplary embodiments comprise computer program instructions which, when executed by a computer such as the onboard computer of a non-contact color measuring spectrophotometer, cause the device or system to change one or more of sensor to sample distance, sensor to sample retention surface distance, absolute sensor position, absolute sample position, relative sensor position, relative sample position, sample movement (e.g., rotation), laser power or gain, illumination spectrum, and other parameters of the system. Exemplary systems may comprise one or more motors and/or controllers for adjusting one or more of the aforementioned parameters or other parameters in response to the execution of the computer program instructions and/or real-time measurements.

According to an aspect of some exemplary embodiments, a color measurement instrument is provided with a controller configured to make automated adjustments of sensor position with respect to a sample (or sample positioning with respect to the sensor). Starting from any distance, a non-contact distance measuring device such as a laser measuring device directs a motorized arm to automatically adjust the sensor position with respect to the sample until a predetermined optimal distance is obtained. Different sample heights and surfaces may result in the system moving the sensor to different absolute sensor positions. Exemplary embodiments may continue to monitor and adjust sensor to sample distance in real time. Exemplary embodiments may minimize the effects of uneven sample surfaces and other sources of changing sensor to sample distances which would ordinarily introduce error into color measurements.

According to a further aspect of some exemplary embodiments, systems and methods are provided which monitor spectrophotometer readings in real time. Based on changes or preconfigured triggers detected in the monitored measurements, the power of the measurement laser is increased or decreased. For example, detection of comparatively dark samples by the system may result in an increase in the power (gain) of the laser. Detection of comparatively light samples by the system may result in an increase in the power (gain) of the laser.

According to yet another aspect of some exemplary embodiments, systems and methods are provided which adjust the illumination spectrum of a spectrophotometer based on real time readings or measurements. For example, a system may be configured to detect low blue wavelength reflectance and, based on the low level detected, increase the blue component of the illumination spectrum (e.g., through control of individually regulated LEDs of an LED array of the sample illumination source of the spectrophotometer).

According to some exemplary embodiments, a color measurement instrument may comprise a sensor head comprising a color detector for collecting a color measurement of a sample; a distance detector configured to detect a distance between the sensor head and the sample; and a motorized axis operated with a feedback loop to automatically adjust a position of the sensor head based on the distance detected by the distance detector. The motorized axis may be configured to adjust the distance entirely independent of human intervention. The distance detector and motorized axis may be configured to continually monitor and adjust the distance of the sensor head to the sample in real time so as to minimize effects of uneven sample surfaces as a source of changing sensor head to sample distance. The instrument may further comprise a turntable configured for rotation of the sample concurrent with the continual monitoring and adjustment of sensor head to sample distance. The instrument may further comprise an LED array for emitting electromagnetic radiation detectable by the color detector as a reflectance of the sample, and one or more lasers for emitting electromagnetic radiation detectable by the distance detector when reflected from the sample. The instrument may further comprise one or more of an onboard computer, a signal conversion module, and a spectrometer system which comprise one or more processors configured to perform signal processing of the signals received from the distance detector and color detector. The one or more lasers may be configured with variable gain, and the one or more processors are configured to increase or decrease real time gain of the one or more lasers based on changes in sample darkness or lightness. The LED array may be configured with an adjustable illumination spectrum, and the one or more processors may be configured to adjust the illumination spectrum of the LED array based on color measurements of the color detector. One or more distance measurements from the distance detector and one or more reflectance measurements from the color detector may be acquired and stored in data pairs by the one or more processors. At least one of the one or more of onboard computer, signal conversion module, and spectrometer system may be configured to adaptively adjust one or more of turntable speed, illumination spectrum, laser gain setting, number of measurement samples, duration of sampling, sample color measurement threshold, and distance variation measurement threshold.

According to some exemplary embodiments, a method of performing non-contact color measurements may comprise collecting a color measurement of a sample with a color detector of a sensor head; detecting a distance between the sensor head and the sample with a distance detector; and operating a motorized axis with a feedback loop to automatically adjust a position of the sensor head based on the distance detected by the distance detector. Adjusting of the distance by the motorized axis may be entirely independent of human intervention. The method may comprise continually monitoring and adjusting the distance of the sensor head to the sample in real time with the distance detector and motorized axis so as to minimize effects of uneven sample surfaces as a source of changing sensor head to sample distance. The method may comprise rotating the sample with a turntable concurrent with the continual monitoring and adjustment of sensor head to sample distance. The method may comprise, with an LED array, emitting electromagnetic radiation detectable by the color detector as a reflectance of the sample, and, with one or more lasers, emitting electromagnetic radiation detectable by the distance detector when reflected from the sample. The method may comprise signal processing of the signals received from the distance detector and color detector with one or more processors of one or more of an onboard computer, a signal conversion module, and a spectrometer system. The method may comprise increasing or decreasing real time gain of the one or more lasers based on changes in sample darkness or lightness. The method may comprise adjusting the illumination spectrum of the LED array based on color measurements of the color detector. The method may comprise acquiring and storing by the one or more processors one or more distance measurements from the distance detector and one or more reflectance measurements from the color detector in data pairs. The method may comprise adaptively adjusting one or more of turntable speed, illumination spectrum, laser gain setting, number of measurement samples, duration of sampling, sample color measurement threshold, and distance variation measurement threshold with at least one of the one or more of onboard computer, signal conversion module, and spectrometer system.

According to some exemplary embodiments, a non-transitory computer readable storage medium may comprise computer program instructions which, when executed by one or more processors of one or more of an onboard computer, signal processing module, and spectrometer system of a non-contact color measurement instrument, cause the instrument to perform collecting a color measurement of a sample with a color detector of a sensor head; detecting a distance between the sensor head and the sample with a distance detector; and operating a motorized axis with a feedback loop to automatically adjust a position of the sensor head based on the distance detected by the distance detector.

DETAILED DESCRIPTION

Figure 1:
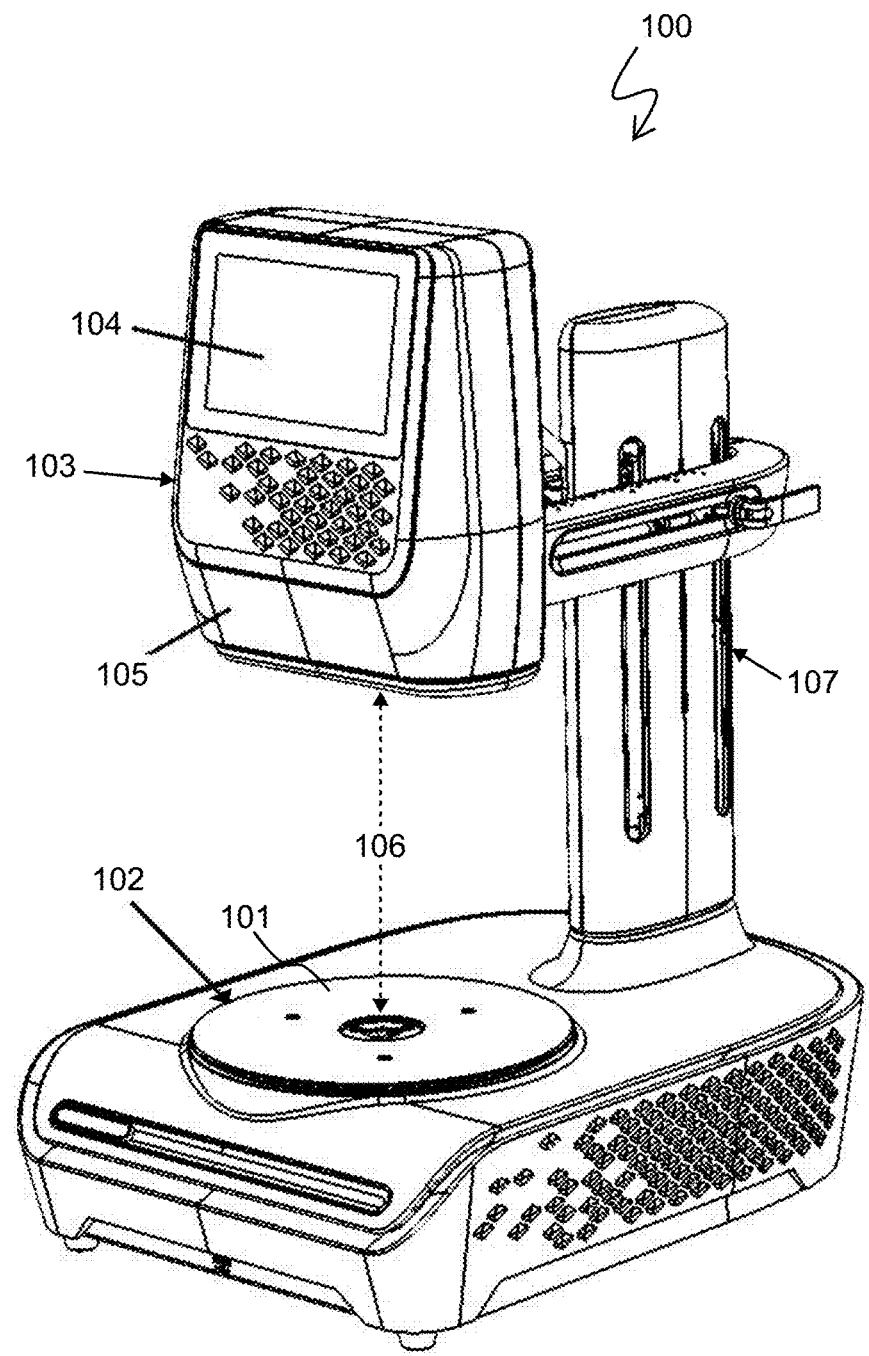
FIG. 1 is a color measurement device at a first distance position.

FIG. 1 shows an exemplary color measurement device 100 (e.g., instrument). The device 100 comprises a surface 101 for arranging samples (e.g., of a rotating sample turntable 102). The device 100 further comprises a sensor module 103 that includes a sensor user interface 104 and a sensor head 105. Note that in some of the descriptions herein "sensor" may be used to refer to "sensor head". The sensor module 103 is set at a distance 106 from the sample turntable 102 by a movable (e.g., motorized) vertical axis 107. The sensor module 103 may be moved to any distance within a range of distances from the sample turntable 102.

Figure 2:
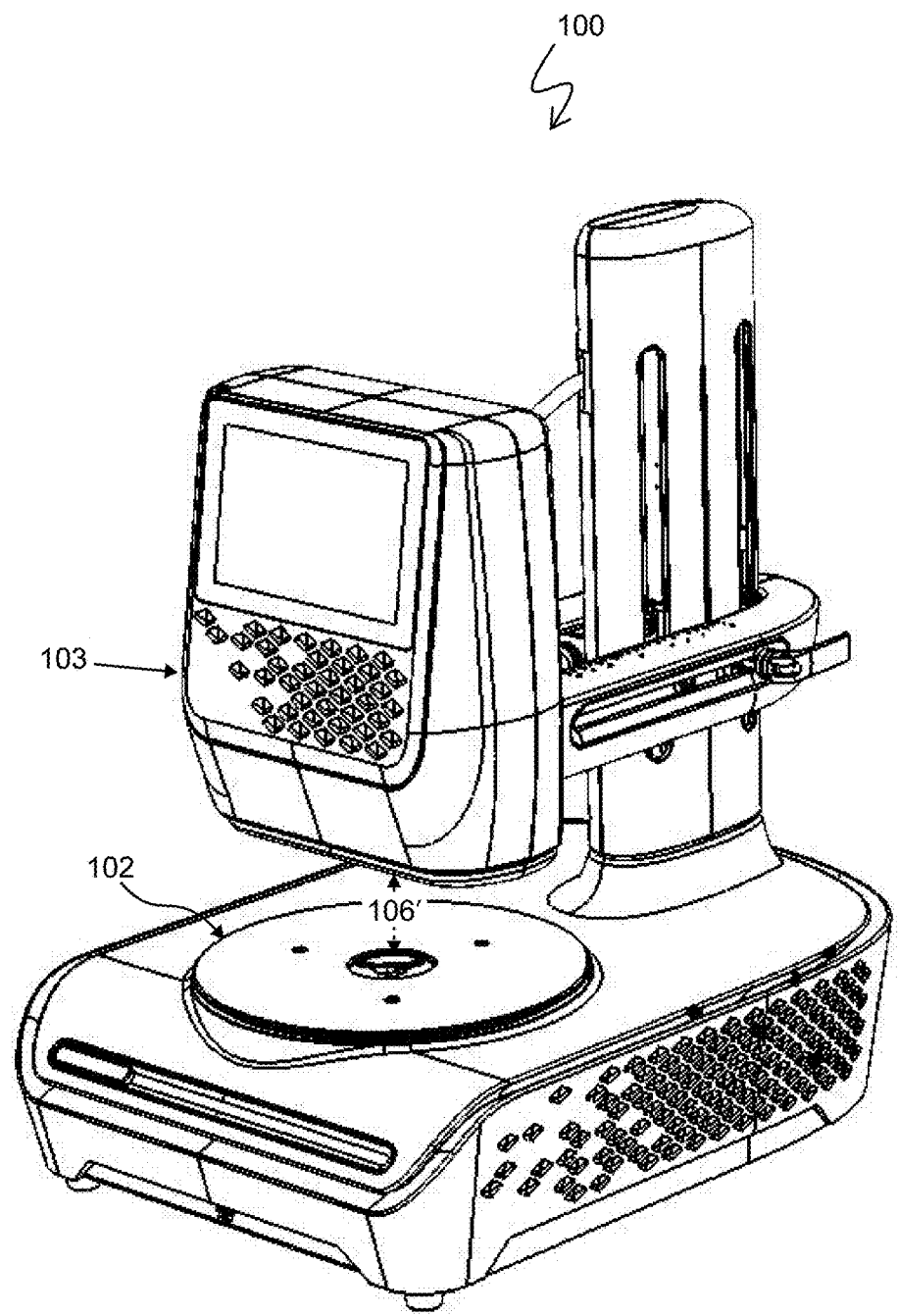
FIG. 2 is the color measurement device at a second distance position.

FIG. 2 shows the color measurement device 100 of FIG. 1 after an adjustment in the position of the sensor module 103. The sensor module 103 is shown in a lower position (e.g., at a closer distance 106' to any sample placed on the sample turntable 102).

The decision as between a device configuration at distance 106 (FIG. 1), a distance 106' (FIG. 2), or some other distance within the operating range of the device 100 is dependent upon the sample to be measured. The device 100 is configured as a multi-application device automatically adaptive and adjustable to collect accurate color measurements for any of a wide variety of samples that may be arranged on the surface 101, and to automatically adjust to collect accurate color measurements for selective parts of whole samples.

Just a few non-limiting examples of samples for which color measurements may be taken are food items like saltine crackers, bagels, and chocolate chip cookies. Non-food samples are of course also usable, but food is exemplary as an industry where color measurement is common. It may be readily appreciated to a reader of this disclosure that a cracker, a bagel, and a chocolate chip cookie may have considerably different dimensions (e.g., heights or thicknesses). However even for any one of these samples the distance from a sensor head 105 to the surface of the sample may vary considerably depending on the point on the surface of the sample from which measurements are taken. A saltine cracker varies in thickness due to salt crystals and blisters, for example. A bagel varies in thickness from zero thickness (at the hole in the center) to a positive thickness which varies with each increment in the bagel's radial direction. A chocolate chip cookie varies in thickness based on the presence or absence of a chocolate chip at any given point on the cookie's surface. Moreover, for any samples with multiple constituent parts in the sample (e.g., salt crystals and cracker body; raisins in bagel bread; chips in cookie dough), it may be desired or required to collect color measurements of only one constituent part to the exclusion of the other parts. An exemplary instrument 100 provides adaptability to these requirements.

Figure 3:
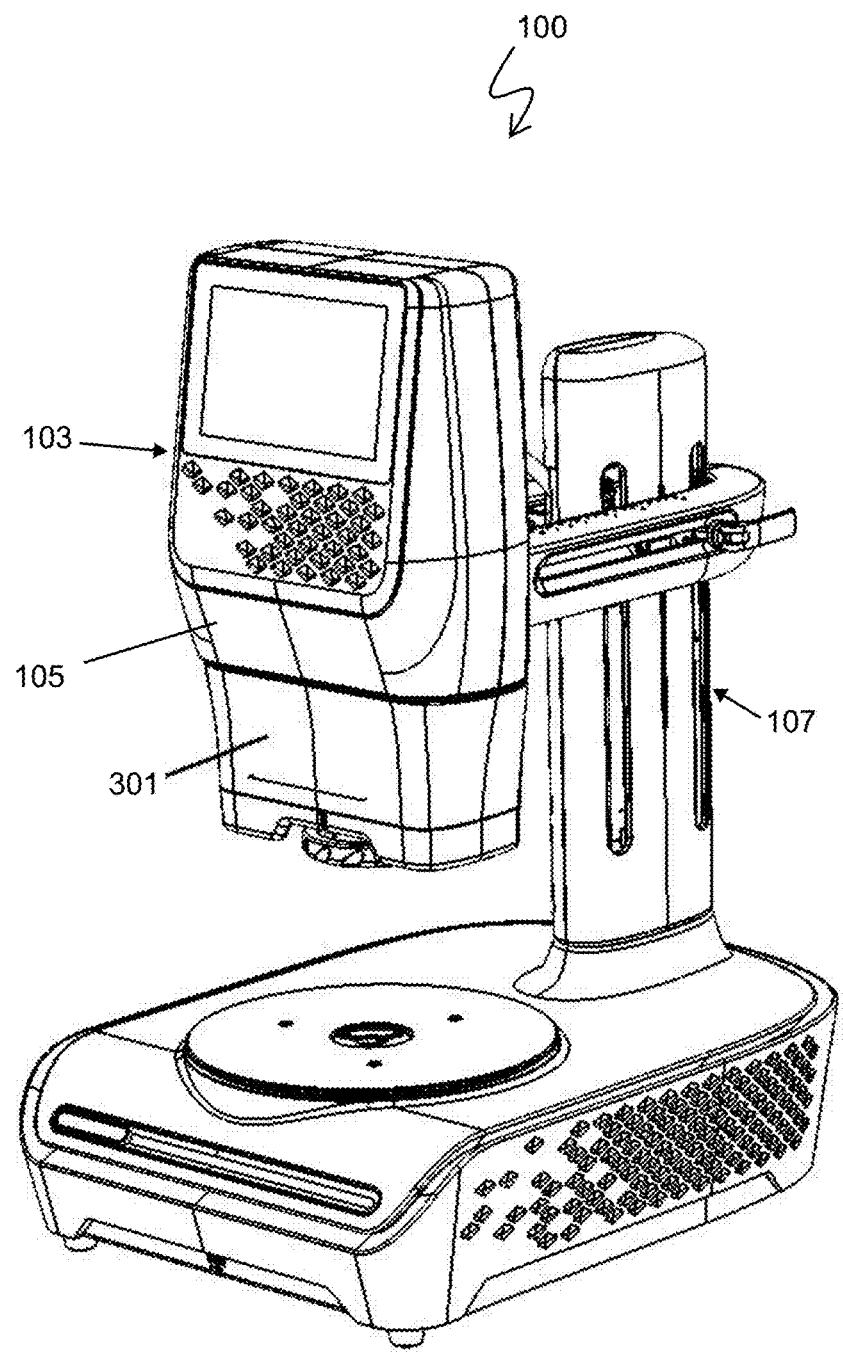
FIG. 3 is the color measurement device with a calibration unit attached.

FIG. 3 shows the sensor module 103 with a calibration unit 301 attached. The calibration unit may magnetically attach to the sensor housing or be attached by other means. The calibration unit 301 enables the insertion of special calibration tiles at a known distance to set the bottom and top of the Grayscale for the instrument 100. The direct attachment of the calibration unit 301 to the sensor head 105 is advantageous in that it eliminates any effect of the position of the moveable vertical axis 107. In other words, regardless of the distance 106, 106', etc. between the sensor head 103 and the sample or turntable 102, the distance between the sensor head 103 and a calibration tile remains constant.

Figure 4A:
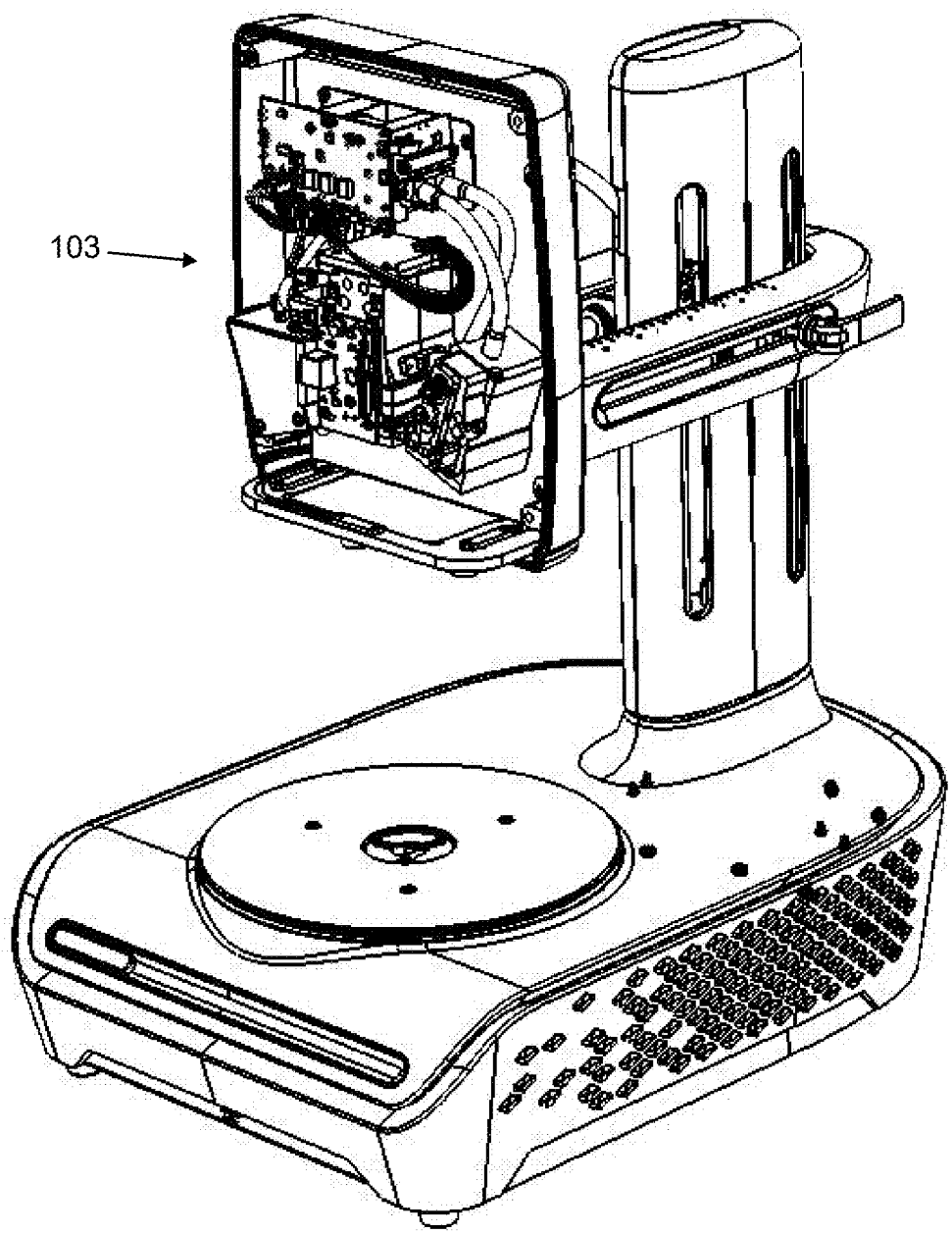
FIGS. 4A and 4B are the color measurement device with external housing and user interface removed from the sensor module for view of device internals.

FIG. 4A shows a cover of the sensor module 103 (including the user interface 104) removed to permit a view of the optical components within the sensor module housing.

Figure 4B:
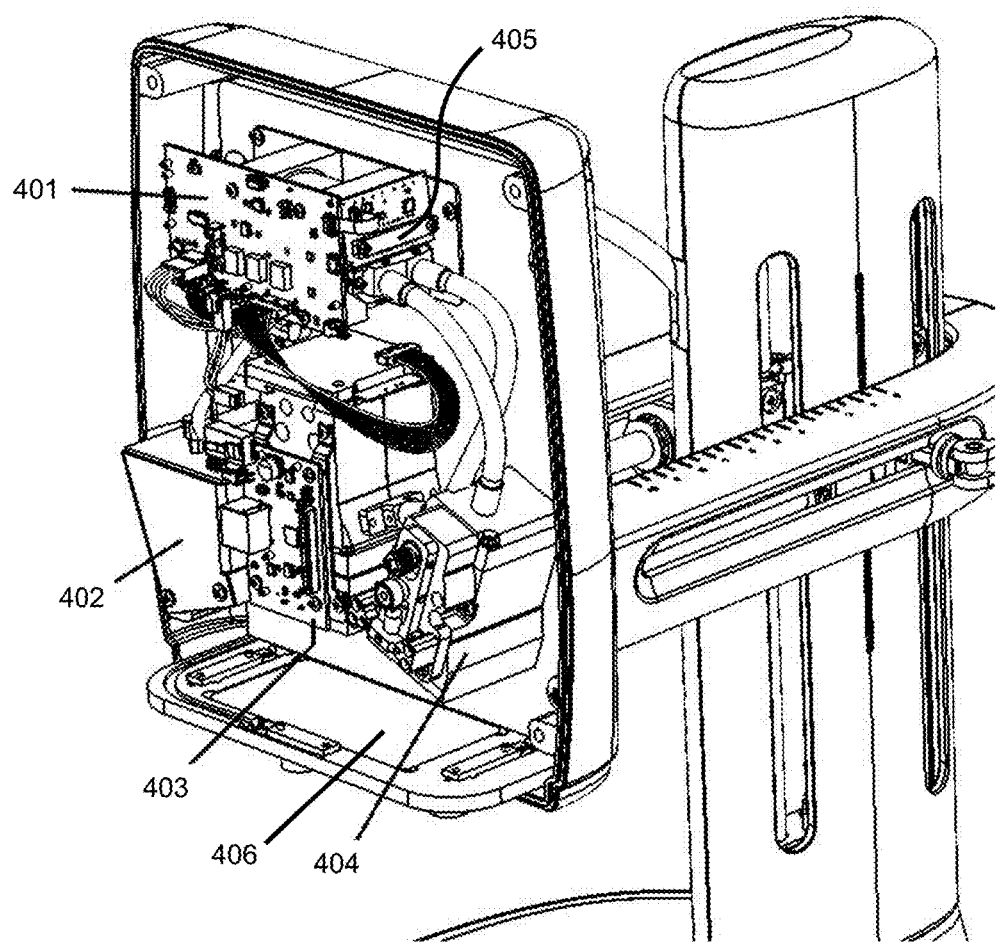

FIG. 4B is a close up of the sensor module internals. The sensor module 103 comprises a signal conversion module/system 401, a distance detector 402, an illumination source 403 (e.g., comprising an LED array and/or one or more lasers), a color detector 404, and spectrometer system 405. The color detector 404 collects signal reflected from the sample and passes it via fiber optic bundles to the spectrometer 405 for characterization. The detectors 402 and 404 may together constitute the sensor head 105. The sensor head 105 may also comprise the illumination source 403 and the optical window 406. The sensor head 105 may also comprise housing.

Some electromagnetic radiation emitted from the illumination source 503 may reflect off a sample, the reflected light being received by the distance detector 502. Other electromagnetic radiation emitted from the illumination source may reflect off the sample, the reflected light being received by the color detector 504. For example, the illumination system may comprise a laser for use together with the distance detector and an LED array for use with the color detector 504 and spectrometer system 505.

Figure 5:
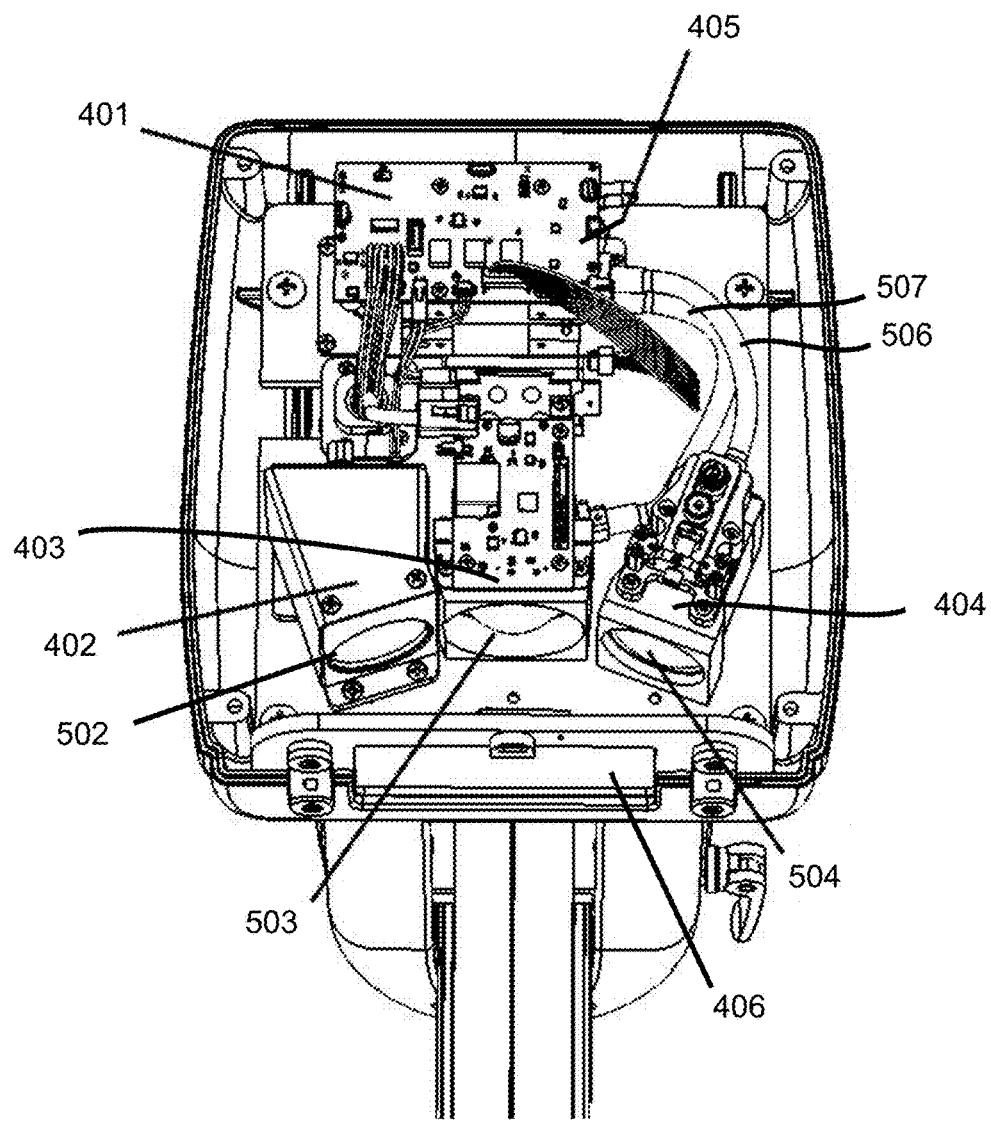
FIG. 5 is another view of the sensor module internals.

FIG. 5 is another close up of internals of the sensor module 103. Lenses 502, 503, and 504 of the distance detector 402, illumination source 403, and color detector 404 are visible, respectively. The signal conversion module 401 (i.e., signal processing module) and spectrometer system 405 are configured to perform signal processing of the signals received from the distance detector 402 and/or color detector 404. A fiber optic cable 506 transfers signals from the color detector 404 to the spectrometer system 405. A second fiber optic cable 507 transfers a reference signal from the illumination source 403 to the spectrometer system 405.

Figure 6:
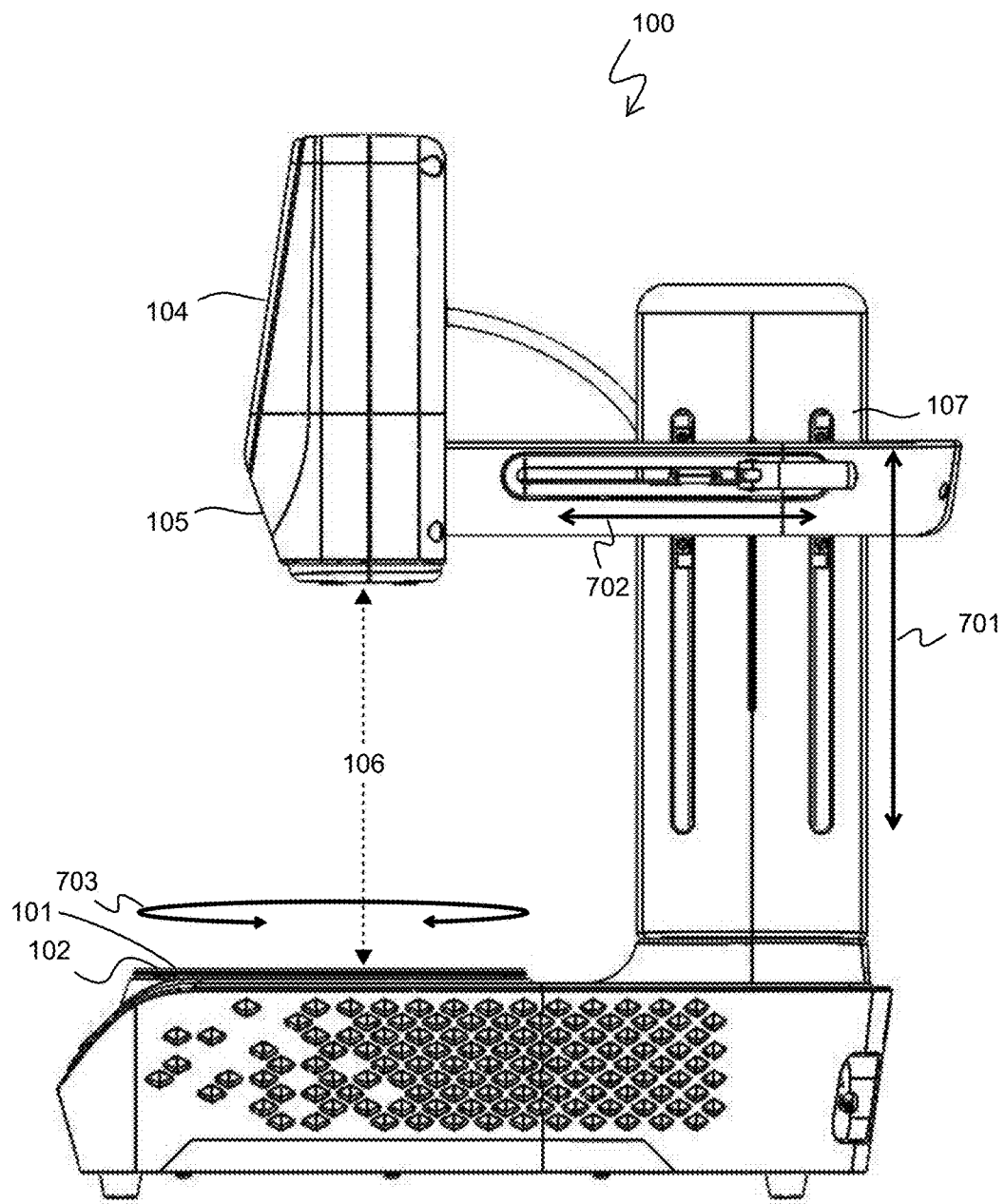
FIG. 6 is a side profile of the color measurement device showing its adjustable spatial axes.

FIG. 6 is a side profile of the color measurement device 100 showing the device's adjustable spatial axes. An exemplary device 100 may automatically and adaptively adjust positioning according to one or more spatial degrees of freedom. In the illustrated embodiment the device 700 is configured for adjustment of the position of sensor head 105 along translational direction 701 (here, the vertical direction) and translational direction 702 (here, the horizontal direction). Arrow 703 indicates a direction of rotation of the turntable 102 which is also controllable by the device 100. In alternative embodiments the surface 101 for receiving the sample may be moveable while a sensor or sensor head remains stationary (or also moves). In any case, separation distances such as the distance 106 may be automatically adjustable before and during measurement protocols under the semi-autonomous or fully-autonomous control of the device 100.

Figure 7A:
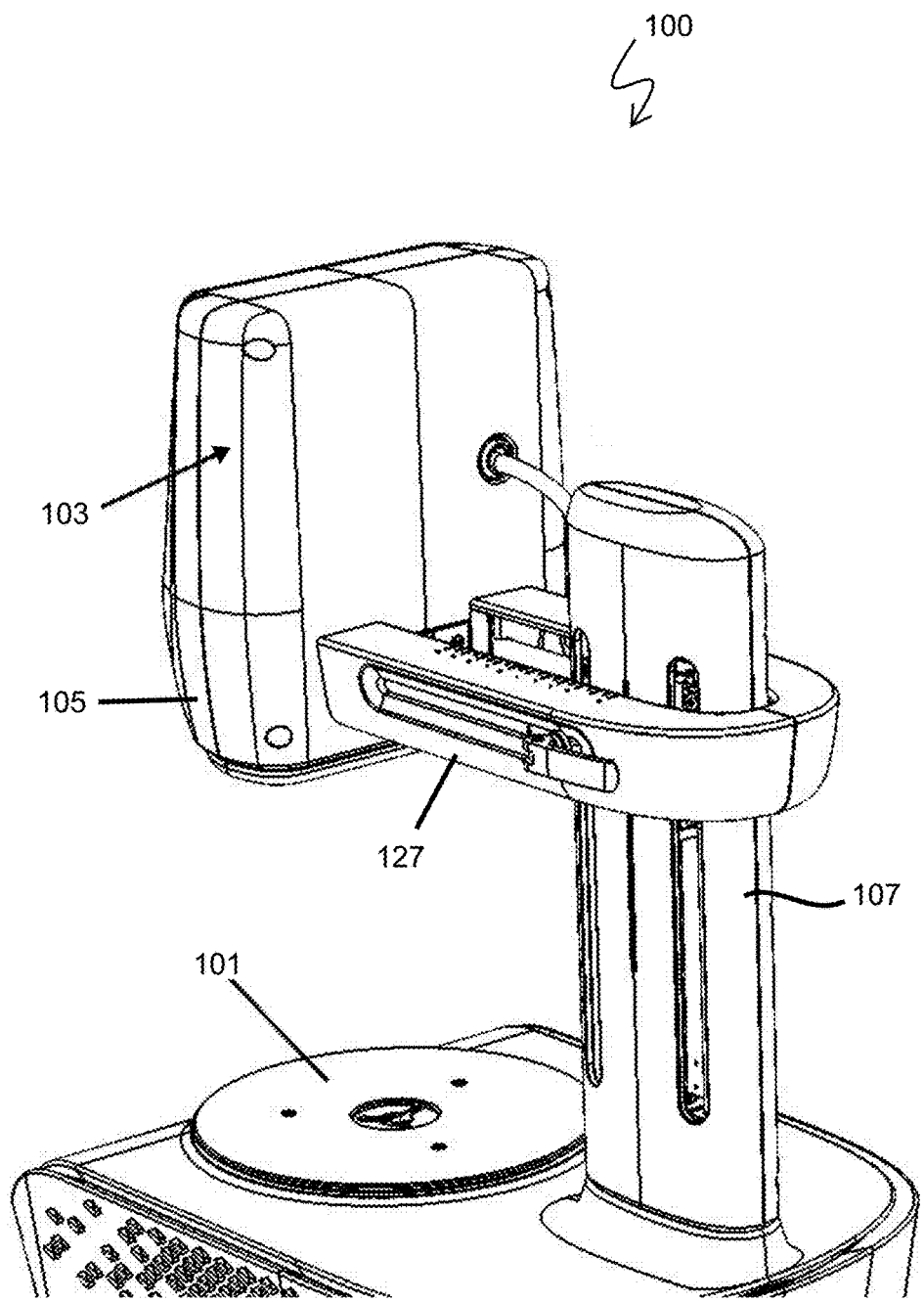
FIG. 7A is the color measurement device's motorized axis at a first position.
Figure 7B:
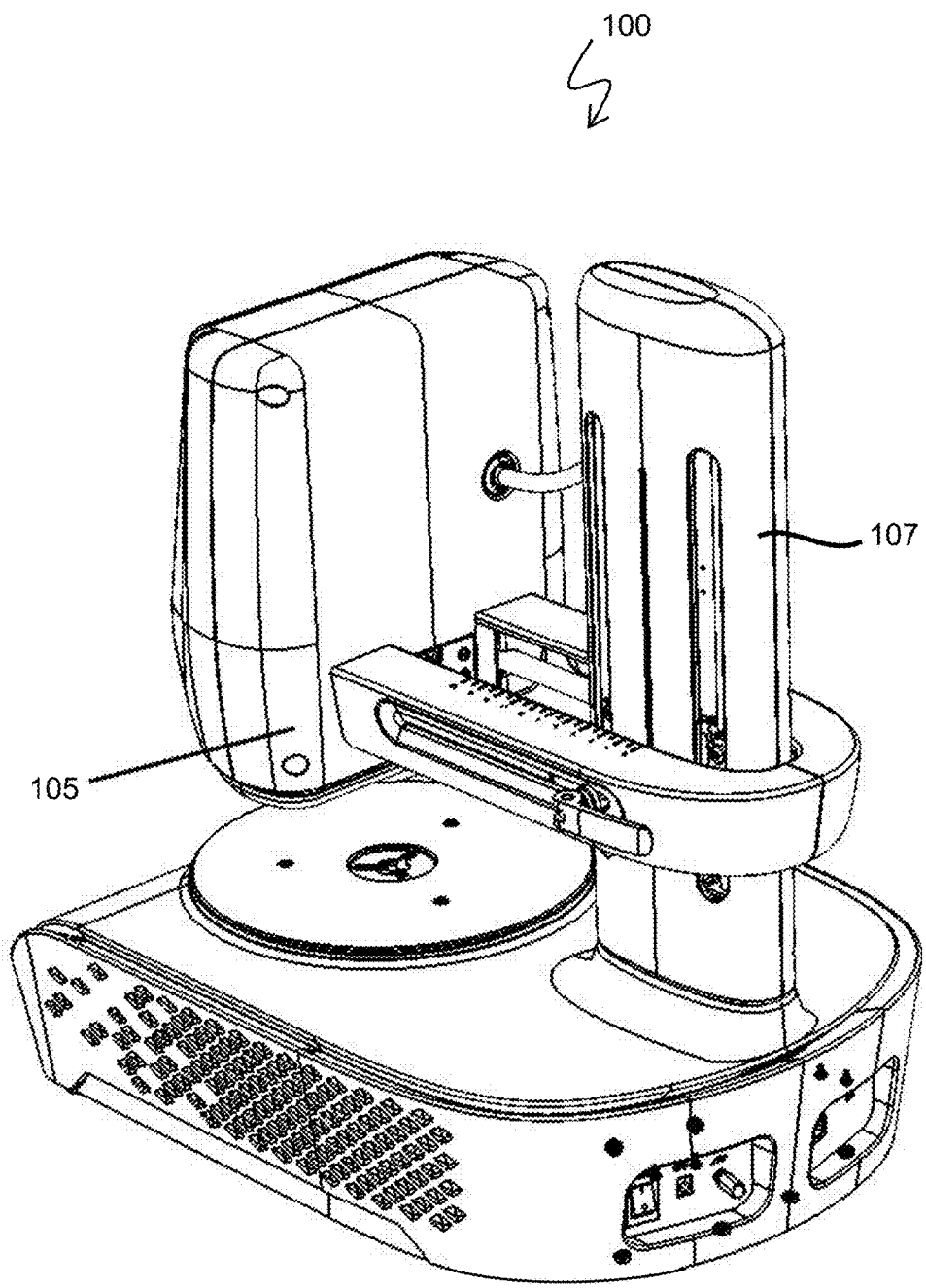
FIG. 7B is the color measurement device's motorized axis at a second position.

FIG. 7A shows a rear facing view of the device 100. The movable axis 107 comprises one or more motors which allow motorized control of the sensor head's vertical position. FIG. 7B is a rear facing view of the device 100 after the sensor head 105 has moved to a lower position on the moveable axis 107 (which may be alternatively referred to as an arm of the device). In the device 100 illustrated by the figures, the vertical axis 107 is substantially parallel with a gravity vector, assuming the device 100 is arranged on a tabletop or similarly flat environmental surface. Indeed, the tabletop configuration of the device 100 is one advantage aspect of this embodiment. It should be appreciated, however, that alternative embodiments of the invention may assume alternation positions with respect to the environment such that the axis separating the sensor head 105 and the surface 101 for arranging samples is not necessarily vertical. The axis may instead be horizontal or at some non-orthogonal angle between vertical and horizontal, for example. In general, the movable axis 107 is normal to the plane of the surface 101.

In some embodiments like device 100 a second movable axis is included. The second moveable axis 127 may be motorized or manual. The second moveable axis 127 is configured to change the point on the surface 101 above which the sensor head 105 is centered. Generally, the second moveable axis 127 may not require any adjustments while color measurements are in progress for a given sample. In contrast, a plurality of adjustments in the moveable axis 107 may be necessary while measuring the given sample.

Figure 8A:
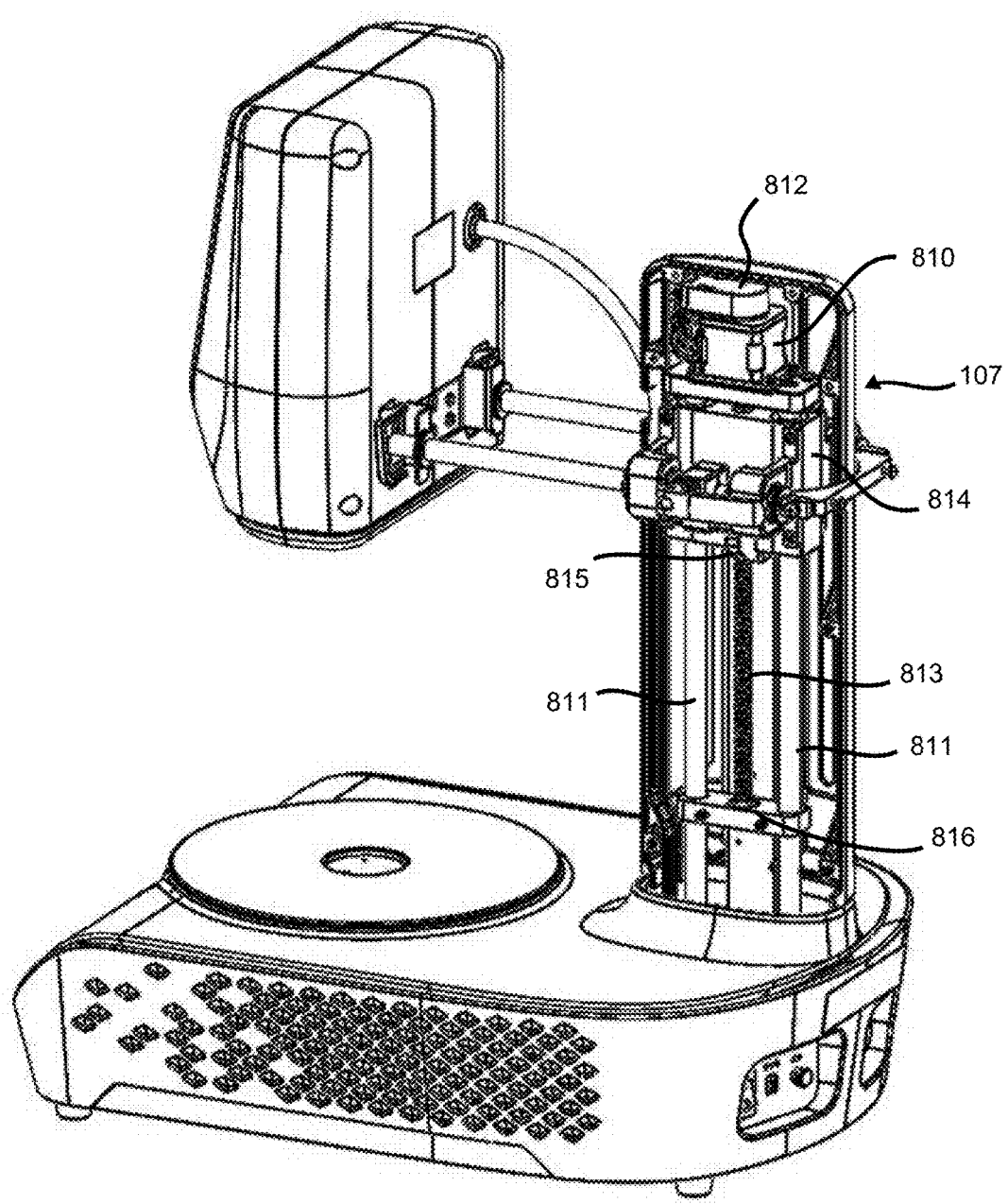
FIGS. 8A and 8B are the color measurement device with housing removed to show internals of the motorized axis.
Figure 8B:
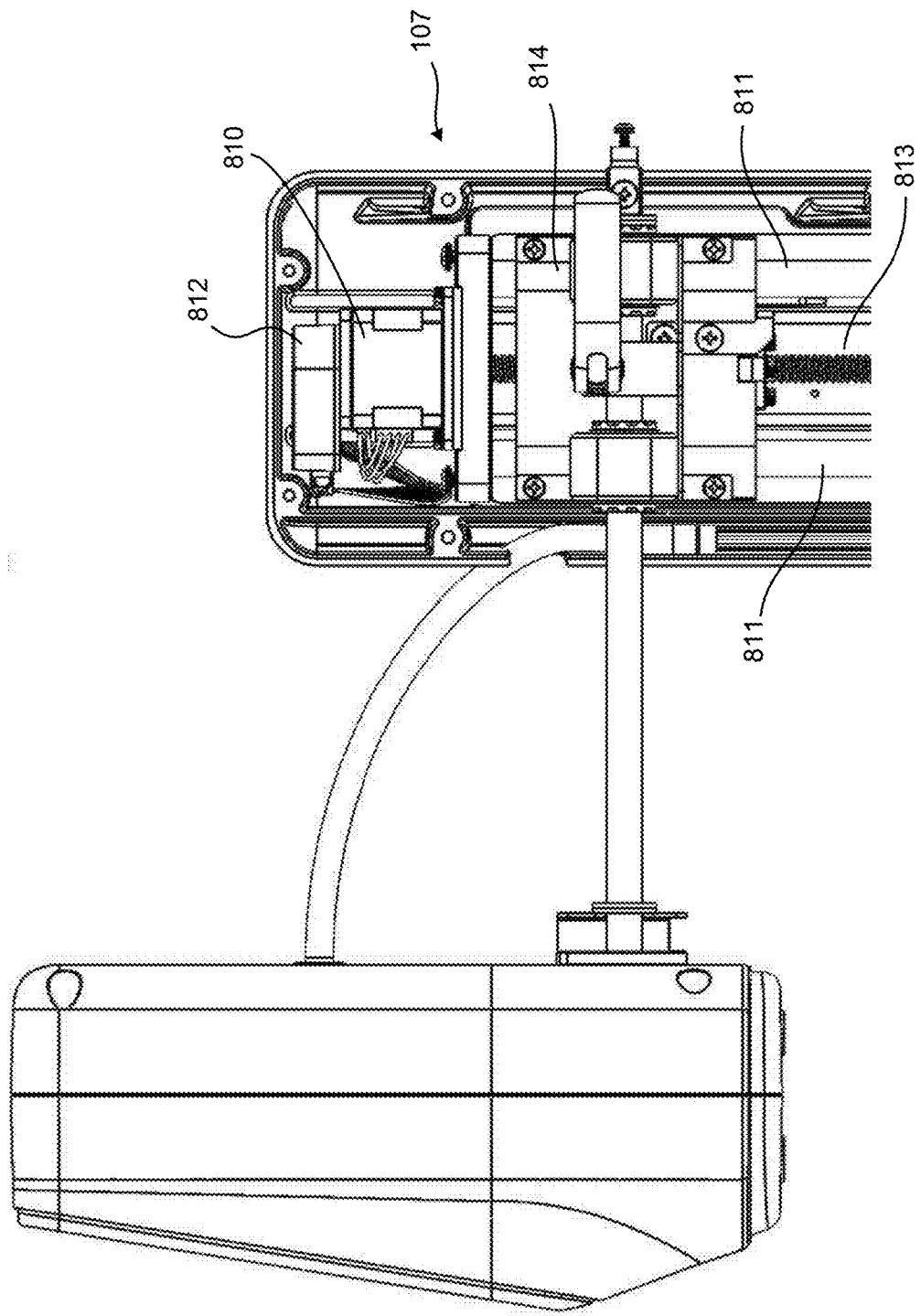

FIGS. 8A and 8B show the motorized axis 107 with housing removed to permit a view of internal components. An exemplary motorized axis 107 may comprise one or more motors 810 (e.g., a stepper motor) and a dedicated rotary position feedback device or encoder 812. The motorized axis 107 may further comprise a mobile stage assembly 814 which translates along a guide rail(s) 811 by rotary motion of the motorized lead screw 813 through the nut 815 rigidly attached to the mobile stage assembly 814. The motorized axis may comprise a gear assembly, e.g., in the mobile stage assembly and/or in the motor assembly. The motorized axis 107 may further comprise other mechanical elements such as a bearing 816.

Figure 9:
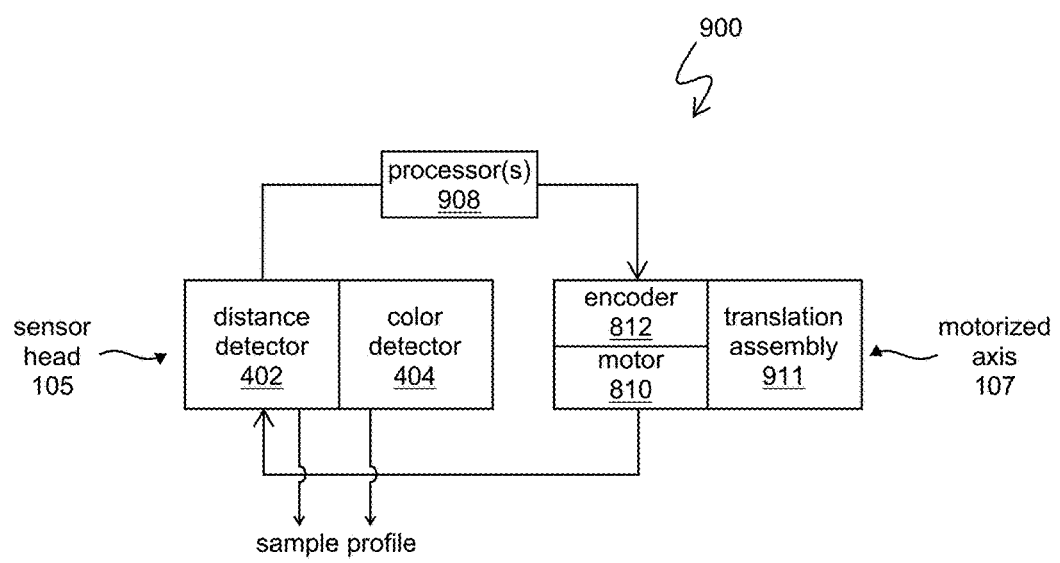
FIG. 9 is a block diagram of the color measurement device feedback loop.

FIG. 9 is a block diagram of a feedback loop 900 for adaptively adjusting the relative distance between sensors and sample. The sensor head 105 comprises the distance detector 402 configured to detect distance between the sensor head 105 and the sample. The sensor head 105 further comprises the color detector 404 for collecting color measurements of the sample. The motorized axis 107 comprises one or more motors 810 and a translation assembly 911 (generally comprising the mobile stage assembly 814, guide rails 811 and lead screw 813 according to the exemplary embodiment depicted in FIGS. 8A and 8B). The motorized axis may also comprise a dedicated encoder 812, e.g., as is common in precision actuators like servomotors. The motorized axis 107 operates with a feedback loop to automatically adjust the distance between the sensor head 105 and the sample based on the distance detected by the distance detector 402. One or more processors 908 may be involved in signal conversion and transmission between the distance detector 105 and motorized axis 107. Distance measures may be obtained by the distance detector 402 and changes in distance effected by the motorized axis 107 in a continual loop, regulated by the one or more processors 908 (e.g., as described below). Adjusting the distance may be implemented by adjusting a position of the sensor head, adjusting a position of the sample, or both.

Figure 10A:
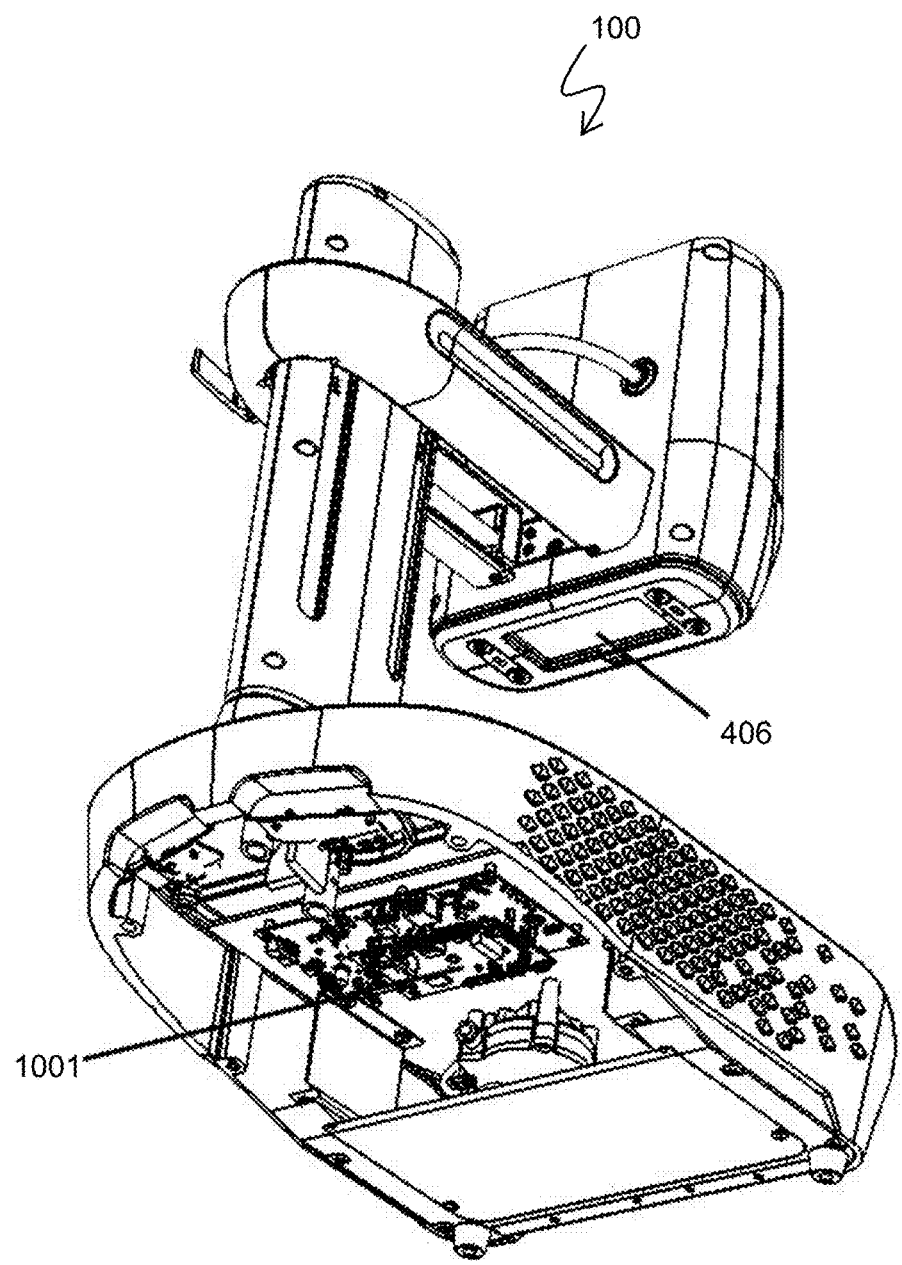
FIG. 10A is the color measurement device with a bottom housing portion removed to show an onboard computer.

FIG. 10A shows a view of the device 100 with a bottom housing portion removed to permit visibility of an onboard computer 1001. The computer is communicatively coupled (e.g., by a wired or wireless connection) to the signal conversion/signal processing module 401 and the spectrometer system 405. The computer 1001 comprises one or more processors configured for executing computer program instructions in accordance with the teachings herein. Processing described herein may be divided among the computer 1001, the signal processing module 401, and the spectrometer system 405.

Figure 10B:
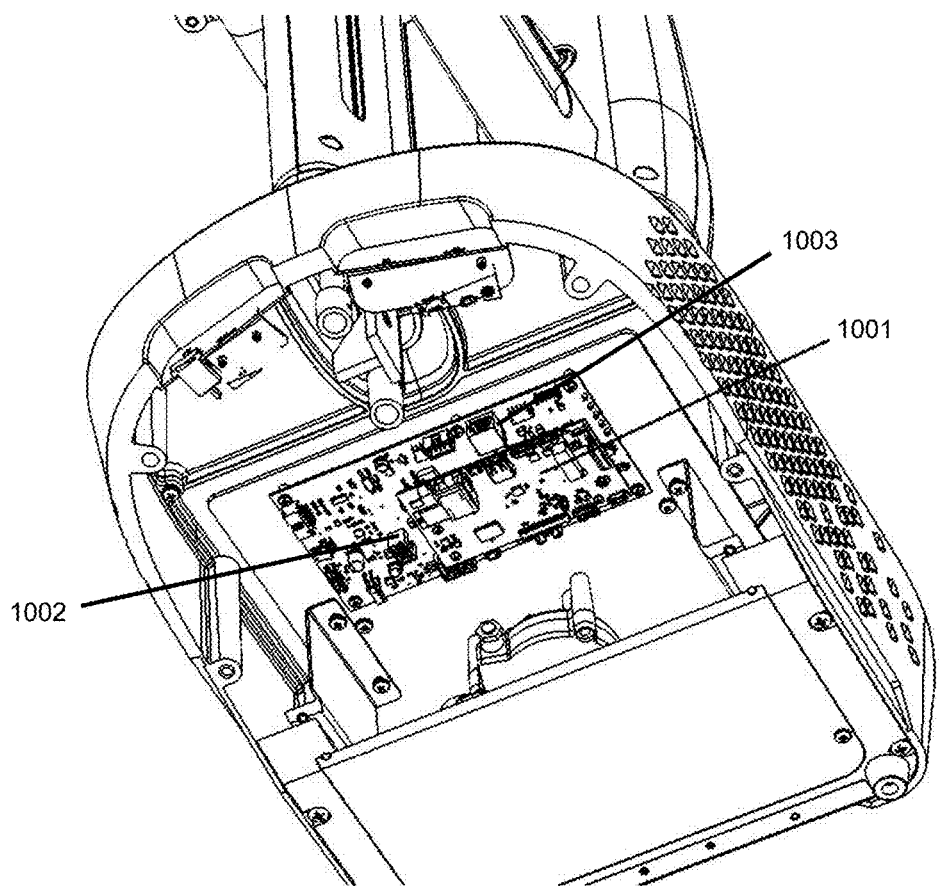
FIG. 10B is a close-up of the color measurement device with visibility of the onboard computer.

FIG. 10B shows a close up of the bottom of the device with a view of the onboard computer. The onboard computer may comprise and/or be connected with one or more storage media (shown generally at 1002) and input/output devices (shown generally at 1003). The storage media 1002 may comprise instructions for execution by the one or more processors.

One or more of the onboard computer 1001, the signal processing module 401, and the spectrometer system 405 may be configured to perform any one or combination of the following:

adjust a height/position/location/distance of the sensors/sensor module based on the real time distance detected between the sensors and a surface of a sample below the sensors, adjust a power or gain of a light emitting component based on (e.g., in dependence on) real time or substantially real time distance or sample readings as detected by one or more of the detectors and processed by the signal processing system and/or the spectrometer system, adjust the illumination spectrum of the illumination system based on (e.g., in dependence on) real time or substantially real time reflectance measurements detected by the color detector.

The adjustments may be semi-autonomous or fully autonomous. The adjustments may be made entirely independent of user/human intervention. Sampling and adjustments during sampling may be conducted with partial automation or full automation. Adjustments in distance/location of the sensor module may be continuous during part up to an entirety of a sample measurement period. The adjustments may be made to counteract any deviations from a preset or predetermined optimal distance. The adjustments may serve to maintain a constant distance. Adjustments in height of the sensor module may occur whenever one or more other variables change during the measurement period. For example, an ongoing feedback loop may exist between the motorized vertical axis and the distance detector, facilitated/managed by the signal processing module and/or the onboard computer.

Figure 11:
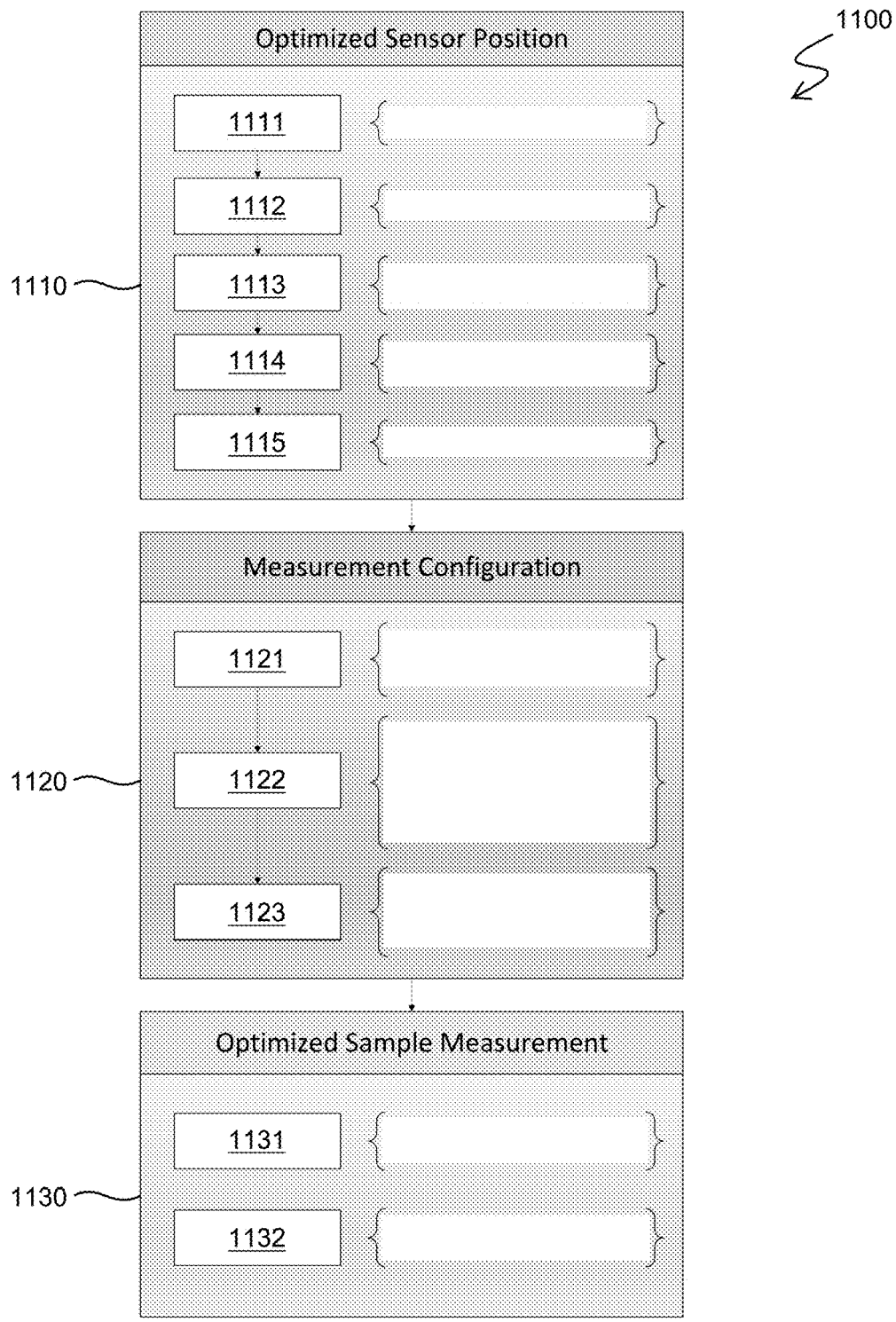
FIG. 11 is an exemplary method for taking color measurements.

FIGS. 11 to 14 depict a method 1100 and subprocesses thereof for collecting color measurements according to an exemplary embodiment. Generally, as shown in FIG. 11, method 1100 may be described according to three stages of activity: optimizing sensor position (block 1110), configuring measurement parameters (block 1120), and optimizing sample measurement (block 1130). The following explanations of method 1100 may refer to various components of the color measurement device 100 illustrated by the preceding figures. Device 100 is an exemplary physical embodiment for performance of exemplary method 1100. Other devices and systems may also be used, as may alternative methods.

Figure 12:
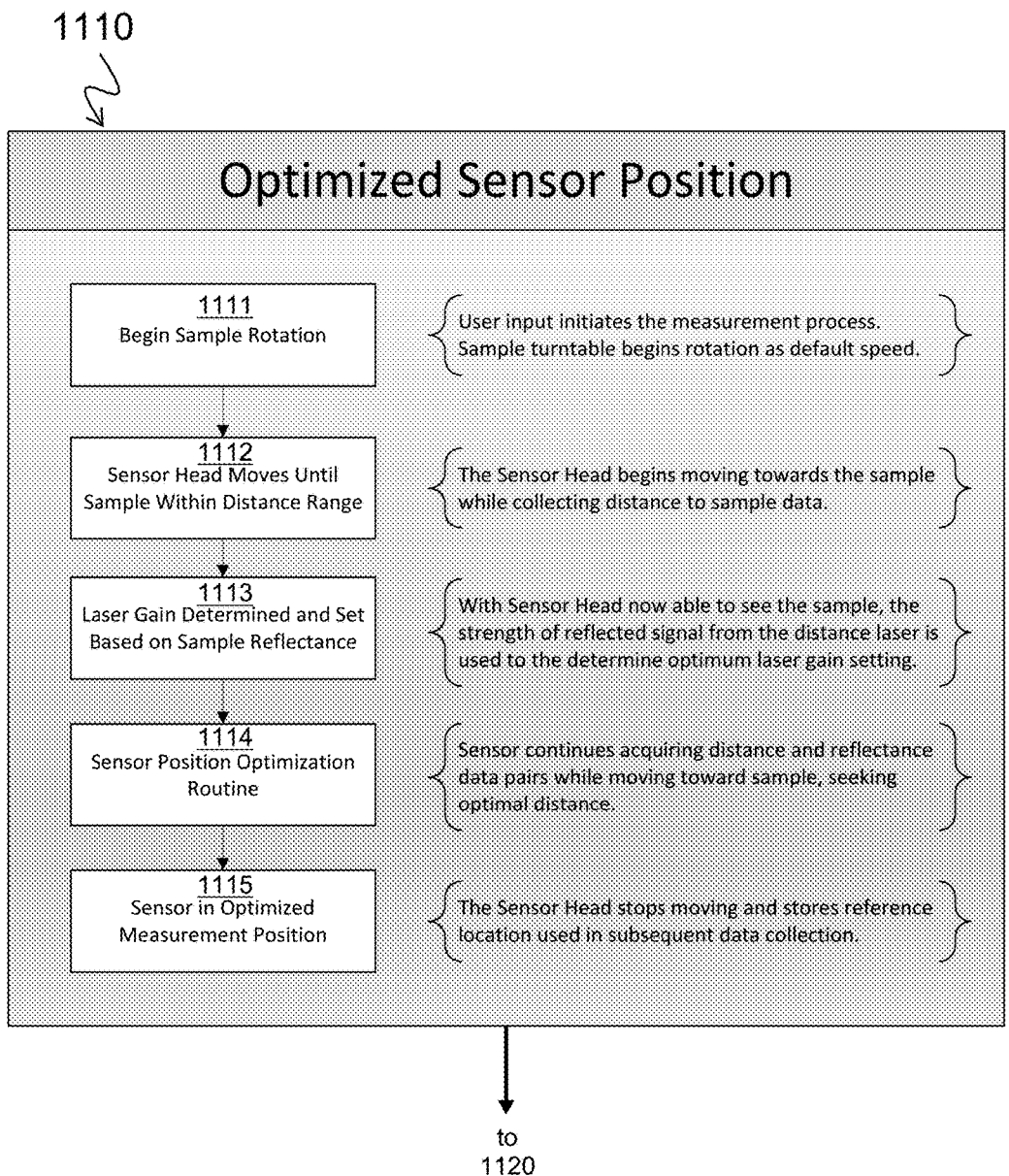
FIG. 12 is an exemplary subroutine to the first stage of the method of FIG. 11.

FIG. 12 shows the subprocess 1110 for optimizing sensor position. The subprocess 1110 may start with sample rotation at block 1111. After the sample to be measured is arranged at the surface 101, a user (e.g., a human employing a color measurement device 100 to characterize a sample) initiates the measurement process via the user interface 104 and the turntable 102 supporting the sample is directed to begin rotation at a default predetermined speed. Note that in some embodiments some samples may not be subject to rotation.

The sensor head 105 begins to move at block 1112 until the sample is within a predetermined distance range as detected by the distance detector 402. Block 1112 may start with the sensor head 105 at an upper or maximum limit of sensor-to-sample distance and incrementally reduce the distance by moving the sensor head 105 while taking a series of distance measurements with the distance detector 402. At too great of distances the distance detector 1112 may collect zero, negligible, or sub-predetermined threshold levels of reflected laser signal from the illumination source 403. Block 1112 may continue (e.g., the sensor head 105 may continue to gradually or incrementally approach the sample) until the amount of reflectance from the one or more lasers of illumination source 403 exceeds some predetermined threshold. Block 1112 serves to move the sensor head 105 until it is able to "see" the sample.

With the sensor head 105 now able to see the sample, the strength of reflected signal from the distance laser is used to determine optimum laser gain setting at block 1113. The optimum laser gain setting may be a function of one or more surface properties of the sample, such as the texture or gloss.

The distance adjustments of block 1112 and the laser gain adjustments 1113 may be interrelated or interdependent. Block 1114 is a routine of optimizing both parameters in tandem. The device 100 may continue acquiring successive distance reflectance data pairs while changing the sensor-to-sample distance (e.g., while reducing the sensor-to-sample distance; while moving the sensor head toward the sample). In other words, according to the organization structure of the flowchart in FIG. 12, block 1114 constitutes a concurrent repetition of blocks 1112 and 1113. The culmination of blocks 1112 to 1114 is block 1115, at which the device 100 reaches an optimized measurement position. At block 1115 the sensor head 105 may (temporarily) stop moving and store reference location (of the sensor head 105) used in subsequent data collection. At the end of 1110, the sensor (head) is located in the optimum position for the loaded sample. The laser gain is also set, and that parameter may be used for subsequent stages and steps.

Figure 13:
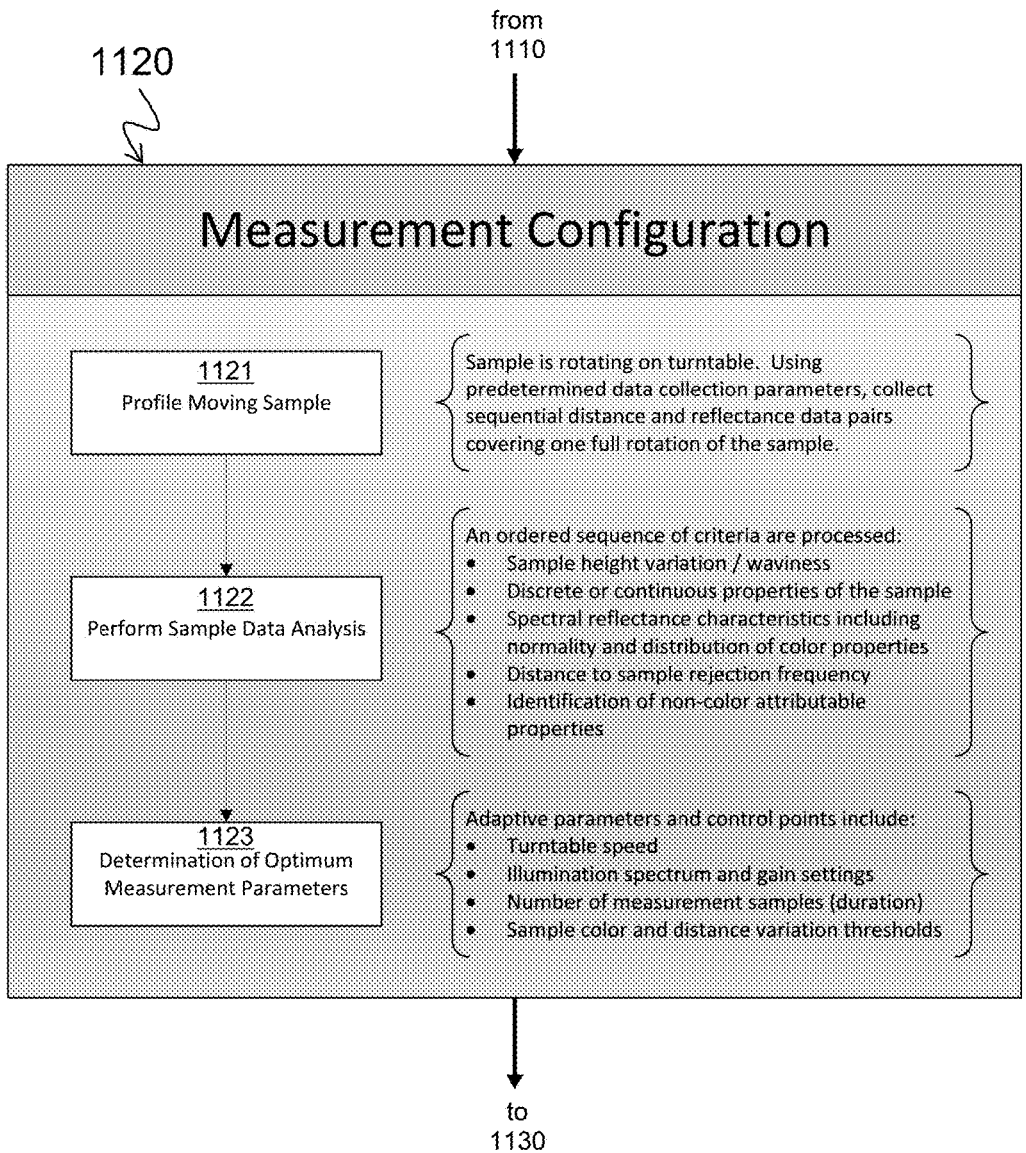
FIG. 13 is an exemplary subroutine to the second stage of the method of FIG. 11.
Figure 14:
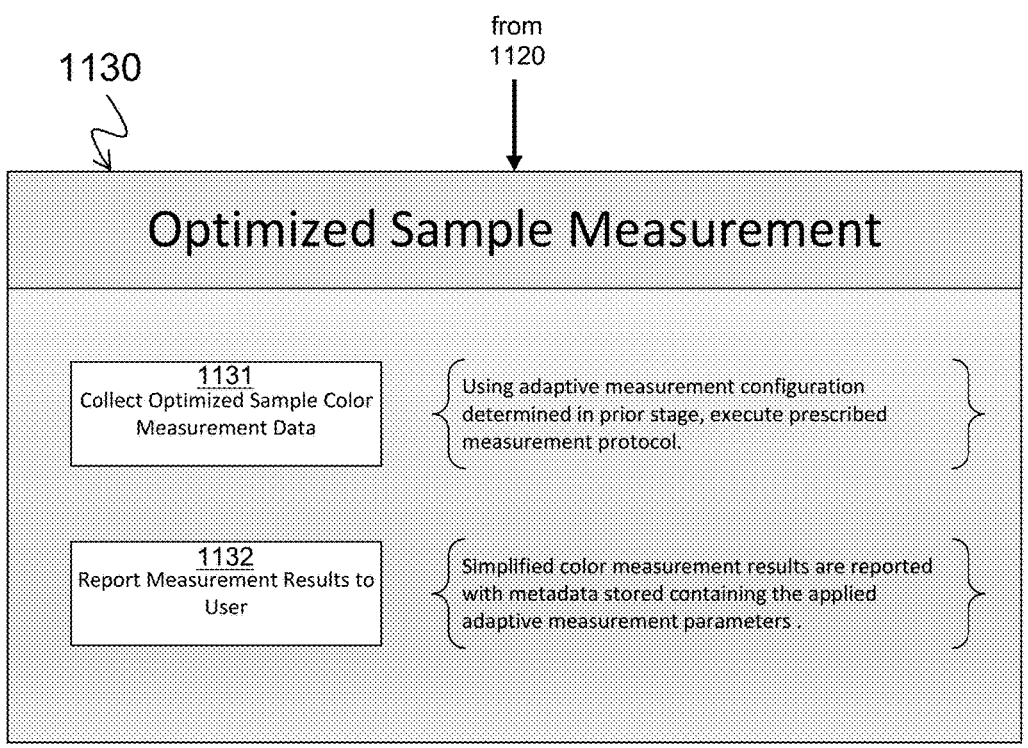
FIG. 14 is an exemplary subroutine to the third stage of the method of FIG. 11.

Method 1100 continues from stage 1110 to stage 1120, shown in FIG. 13. Stage 1120 comprises configuring measurement parameters. A moving sample is profiled at block 1121. This may entail rotating the sample on the turntable 102 for one full rotation or a plurality of rotations depending on a user-determined setting (e.g., 1, 2, 3, 4, 5 or more, 10 or more, etc. rotations). Using predetermined data collection parameters from stage 1110 (e.g., the set laser gain), sequential distance and reflectance data pairs are collected for the full rotation of the sample. The distance data is collected with the distance detector 402. Concurrently, reflectance data (in particular spectral, i.e., color data) is collected with the color detector 404. A single rotation may yield a plurality (e.g., 30, 40, 50, 60, or more) data pairs, for example, which altogether may be stored as a sample "profile". Collecting the distance and reflectance data in pairs permits subsequent application of the distance data to correct output color data. In some embodiments distance and reflectance are always collected in pairs.

Next, sample data analysis is performed at block 1122. The criteria processed may be an ordered sequence of one or more (e.g., all) of the following: sample presentation orientation, sample shape/structural characteristics, sample surface and height variability, discrete or continuous nature of the sample, spectral reflectance characteristics including normality and distribution of color properties, sample distance rejection frequency, and identification of non-color attributable properties.

Sample presentation orientation refers to samples such as potato chips that may be lying flat in the sample pan or on edge or some position in between. Sample shape characteristics may include, for example, small donut-style cereals that have a center hole or unique extruded shapes such as cheese curls. Sample height variation is represented by the curvature of a muffin top or loaf of bread, for example. A discrete sample is one characterized by a placement of some countable number of similar products that are positioned such that they do not overlap or create a contiguous sample pattern, for example an array of sugar cookies or snack wafers in a pan. In contract, a continuous sample is typically comprised of countless smaller samples that are measured in bulk by dumping them into a sample pan, e.g. beans, coffee ground, pellets, or granules. The normality and distribution of spectral reflectance characteristics are useful in identifying samples that have non-homogenous color distributions, e.g. a chocolate chip cookie or blueberry muffin both of which have a base color and highlights that are detectable. A sample distance rejection occurs when the height measurement of a sample, typically a discrete one, varies beyond the range of interest of the sample, indicating that the sample is no longer in view of the sensor or that the height/distance signal is not usable. A non-color attributable property is one that is not directly related to the sample color properties of interest, for example, the color of the pan containing the samples.

Next, optimum measurement parameters are determined at block 1123. Adaptive parameters and control points may include one or more (e.g., all) of the following: turntable speed, illumination spectrum and gain settings, number of measurement samples (duration), and sample color and distance variation thresholds. These parameters and control points are "adaptive" in that the device 100 is configured to select and adjust value(s) for one or more of the parameters or control points based on the immediate sample to be measured. The actual values assumed for the parameters and control points are adapted to accommodate the potentially unique or particular qualities of a given sample. As between two samples which are different (e.g., a potato chip and a slice of bread) the adaptive parameters and control points may take different values in accordance with exemplary color measurement methods (e.g., method 1100).

At stage 1130, and in particular at block 1131, the device 100 executes the prescribed measurement protocol determined at stage 1120. The measurement protocol has been adapted to the present sample or sample type and thus uses the adaptive measurement configuration and parameters determined in stage 1120. The raw data produced by the measurement process of the device 100 may be stored and/or output to a user. In many cases users may require only some of the available data generated. At block 1132, measurement results are output to a user. Simplified color measurement results may be reported while metadata containing all details of the applied adaptive measurement parameters are stored for optional use.

A difference between the two stages 1120 and 1130 is that stage 1120 is measuring, studying, and analyzing the sample that is presented to the instrument. Once the "profile" is collected and analyzed, the instrument is configured a certain way to then take an optimized measurement at stage 1130. The parameters of block 1123 are used in block 1131 where the final data is collected and the answer computed and then presented at block 1132.

The sensor at stage 1130 is executing the optimum measurement of the exact presented sample. For example, the sample presented at step 1111 is the same sample, untouched or disturbed, at the time of the final measurement at step 1131. As an illustrative example, one may imagine a tray of tortilla chips. The chips are laid out in a specific random way, and the instrument profile will be trained upon the details of that sample in that exact configuration. If a user were to rake her hand through the chips and re-level it or shake it up, this disturbance would have the effect of creating a new sample in actuality.

The present invention may be a system, a method, and/or a computer program product. The computer program product may include a computer readable storage medium (or media) having computer readable program instructions thereon for causing a processor (or processors) to carry out aspects of the present invention.

A computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Java, Smalltalk, C++ or the like, and conventional procedural programming languages, such as the "C" programming language or similar programming languages. The computer readable program instructions may execute entirely on a standalone special purpose instrument like device 100, on a user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Some aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions. In addition, while a general logic flow has been illustrated (e.g., in FIGS. 11-14), is not necessary in all embodiments that all blocks are performed or that the blocks are performed in the illustrated order. Some steps may occur in a different order than illustrated. In some embodiments some steps may be omitted or have other intervening steps added. In some embodiments some steps may be performed concurrently. In some embodiments some steps may be performed just once or a plurality of times.

Computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

Other embodiments of the invention may comprise additional features beyond those described in connection with the illustrative embodiment depicted in the figures. Furthermore, other embodiments may comprise fewer than the described features. That is to say, some embodiments may comprise or consist of a subset of the features of the exemplary device shown in the figures. Variations and alternative configurations may occur in the practice of the invention.

What is claimed is:

1. A color measurement instrument, comprising
a sensor head comprising a color detector for collecting a color measurement of a sample;
a distance detector configured to detect a distance between the sensor head and the sample; and
a motorized axis operated with a feedback loop to automatically adjust a position of the sensor head or sample based on the distance detected by the distance detector.

2. The color measurement instrument of claim 1, wherein the motorized axis is configured to adjust the distance entirely independent of human intervention.

3. The color measurement instrument of claim 1, wherein the distance detector and motorized axis are configured to continually monitor and adjust the distance of the sensor head to the sample in real time so as to minimize effects of uneven sample surfaces as a source of changing sensor head to sample distance.

4. The color measurement instrument of claim 3, further comprising a turntable configured for rotation of the sample concurrent with the continual monitoring and adjustment of sensor head to sample distance.

5. The color measurement instrument of claim 1, further comprising
an LED array for emitting electromagnetic radiation detectable by the color detector as a reflectance of the sample, and
one or more lasers for emitting electromagnetic radiation detectable by the distance detector when reflected from the sample.

6. The color measurement instrument of claim 5, further comprising one or more of an onboard computer, a signal conversion module, and a spectrometer system which comprise one or more processors configured to perform signal processing of the signals received from the distance detector and color detector.

7. The color measurement instrument of claim 6, wherein the one or more lasers are configured with variable gain, and the one or more processors are configured to increase or decrease real time gain of the one or more lasers based on changes in sample darkness or lightness.

8. The color measurement instrument of claim 6, wherein the LED array is configured with an adjustable illumination spectrum, and the one or more processors are configured to adjust the illumination spectrum of the LED array based on color measurements of the color detector.

9. The color measurement instrument of claim 6, wherein one or more distance measurements from the distance detector and one or more reflectance measurements from the color detector are acquired and stored in data pairs by the one or more processors.

10. The color measurement instrument of claim 9, wherein at least one of the one or more of onboard computer, signal conversion module, and spectrometer system is configured to adaptively adjust one or more of turntable speed, illumination spectrum, laser gain setting, number of measurement samples, duration of sampling, sample color measurement threshold, and distance variation measurement threshold.

11. A method of performing non-contact color measurements, comprising
    collecting a color measurement of a sample with a color detector of a sensor head;
    detecting a distance between the sensor head and the sample with a distance detector; and
    operating a motorized axis with a feedback loop to automatically adjust a position of the sensor head or sample based on the distance detected by the distance detector.

12. The method of claim 11, wherein adjusting of the distance by the motorized axis is entirely independent of human intervention.

13. The method of claim 11, further comprising continually monitoring and adjusting the distance of the sensor head to the sample in real time with the distance detector and motorized axis so as to minimize effects of uneven sample surfaces as a source of changing sensor head to sample distance.

14. The method of claim 13, further comprising rotating the sample with a turntable concurrent with the continual monitoring and adjustment of sensor head to sample distance.

15. The method of claim 11, further comprising
    with an LED array, emitting electromagnetic radiation detectable by the color detector as a reflectance of the sample, and
    with one or more lasers, emitting electromagnetic radiation detectable by the distance detector when reflected from the sample.

16. The method of claim 15, further comprising signal processing of the signals received from the distance detector and color detector with one or more processors of one or more of an onboard computer, a signal conversion module, and a spectrometer system.

17. The method of claim 16, further comprising increasing or decreasing real time gain of the one or more lasers based on changes in sample darkness or lightness.

18. The method of claim 16, further comprising adjusting the illumination spectrum of the LED array based on color measurements of the color detector.

19. The method of claim 16, further comprising acquiring and storing by the one or more processors one or more distance measurements from the distance detector and one or more reflectance measurements from the color detector in data pairs.

20. The method of claim 19, further comprising adaptively adjusting one or more of turntable speed, illumination spectrum, laser gain setting, number of measurement samples, duration of sampling, sample color measurement threshold, and distance variation measurement threshold with at least one of the one or more of onboard computer, signal conversion module, and spectrometer system.

21. A non-transitory computer readable storage medium comprising computer program instructions which, when executed by one or more processors of one or more of an onboard computer, signal processing module, and spectrometer system of a non-contact color measurement instrument, cause the instrument to perform
    collecting a color measurement of a sample with a color detector of a sensor head;
    detecting a distance between the sensor head and the sample with a distance detector; and
    operating a motorized axis with a feedback loop to automatically adjust a position of the sensor head or sample based on the distance detected by the distance detector.

* * * * *